United States Patent [19]
Fujikawa et al.

[11] Patent Number: 4,746,663
[45] Date of Patent: * May 24, 1988

[54] PYRAZOLO[4,3-D]PYRIMIDINE DERIVATIVE, PROCESS FOR ITS PRODUCTION, AND ANTIHYPERLIPIDEMIC OR ANTIATHEROSCLEROTIC AGENT CONTAINING IT

[75] Inventors: Yoshihiro Fujikawa, Sakura; Mikio Suzuki, Chiba; Mitsuaki Sakashita, Urawa; Nobutomo Tsuruzoe, Kuki; Tadashi Miyasaka, Yokohama, all of Japan

[73] Assignee: Nissan Chemical Industries Ltd., Tokyo, Japan

[*] Notice: The portion of the term of this patent subsequent to Mar. 31, 2004 has been disclaimed.

[21] Appl. No.: 890,549

[22] Filed: Jul. 30, 1986

[30] Foreign Application Priority Data

Aug. 1, 1985 [JP] Japan .................. 60-169987

[51] Int. Cl.⁴ .................. A61K 31/415; C07D 487/04
[52] U.S. Cl. ..................... 514/258; 544/262
[58] Field of Search ............. 544/262, 256; 514/258, 514/405

[56] References Cited
U.S. PATENT DOCUMENTS 4,654,348  3/1987  Fujikawa ............... 514/258

FOREIGN PATENT DOCUMENTS 0073328  3/1983  European Pat. Off. .
0157415  10/1985  European Pat. Off. .

OTHER PUBLICATIONS

Burger, A. *A Guide to the Chemical Basis of Drug Design* (1983) (John Wiley and Sons: New York, N.Y.) p. 15.
Merck Index, 9th ed. (1976), p. ONR-27 (Merck and Co.; Rahway, N.J.).
Physicians' Desk Reference, 40th ed. (1986) (pub: E. Barnhart) p. 881.

Primary Examiner—Donald G. Daus
Assistant Examiner—Mark W. Noel
Attorney, Agent, or Firm—Oblon, Fisher, Spivak, McClelland & Maier

[57] ABSTRACT

A pyrazolo[4,3-d]pyrimidine derivative having the formula:

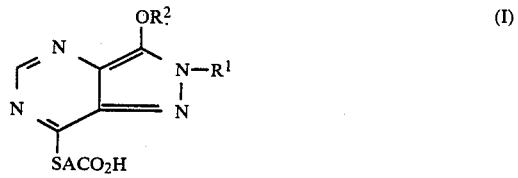

wherein $R^1$ is lower alkyl or phenyl which is unsubstituted or substituted by lower alkyl, lower alkoxy or halogen; $R^2$ is a saturated or unsaturated, straight chain or branched aliphatic group having from 2 to 22 carbon atoms or phenyl-lower alkyl with the phenyl group unsubstituted or substituted by lower alkyl, lower alkoxy or halogen; and A is an alkylene group having from 1 to 3 carbon atoms which is unsubstituted or substituted by methyl, or a pharmaceutically acceptable salt thereof.

12 Claims, No Drawings

PYRAZOLO[4,3-D]PYRIMIDINE DERIVATIVE, PROCESS FOR ITS PRODUCTION, AND ANTIHYPERLIPIDEMIC OR ANTIATHEROSCLEROTIC AGENT CONTAINING IT

The present invention relates to a novel pyrazolo[4,3-d]pyrimidine derivative, a process for its production and an antihyperlipidemic or antiatherosclerotic agent containing it.

Hyperlipidemia (hyperlipemia) is regarded as a major risk factor for the atherosclerosis. Heretofore, a number of antihyperlipidemic agents have been studied. Therapeutic agents in this field are likely to be used for an extended period of time in view of the nature of the diseases, and they are required to be highly safe. However, with respect to nicotinic acid and its derivatives, or clofibrate and its derivatives, which have been widely used as antihyperlipidemic agents, various subsidiary ill effects have been reported, and they can hardly be accepted as satisfactory therapeutic agents. For instance, with respect to nicotinic acid and its derivatives it has been reported that they will bring about e.g. flashing or gastroenteric troubles. With respect to clofibrate and its derivatives, it is known that they will bring about e.g. myalgia or hepatic insufficiency, and they are likely to lead to gallstone formation. Further, it has been reported that clofibrate brings about hepatic carcinoma on animal experiments. [D. J. Svoboda and D. L. Azarnoff, Cancer Res., 39, 3419 (1979)]

In addition to the question of the safety, there has been a progress in the study of the pharmacological activities. Reflecting the progress in the recent years in the study of the lipid metabolism, particularly in the study of the functional mechanism of serum lipoprotein as a transporter of serum lipid, an attention about the effect of the drug has been drawn not only to the activity of the drug to reduce the lipid concentration in serum but also to the effect to the lipoprotein. Serum cholesterol constitutes the lipoprotein together with triglyceride, phospholipid and apoprotein. This lipoprotein is generally classified into Cyromicron, VLDL (very low density lipoprotein), LDL (low density lipoprotein) and HDL (high density liprotein) depending upon the difference in the specific gravity. Among these, Cyromicron, VLDL and LDL are believed to be the lipoproteins which induce atherosclerosis. Whereas, HDL is believed to have functions to transport cholesterol from peripheral blood vessels to a liver, to form a cholesterol ester or to contribute to the catabolism of triglyceride, and thus serves for the prevention and regression of the atherosclerosis. Accordingly, for an antihyperlipidemic agent to be developed, it is desired that such an agent has not only the function to reduce the total value of serum cholesterol, but also the functions to reduce LDL-cholesterol and to increase HDL-cholesterol.

The present inventors have conducted various researches for compounds having antihyperlipidemic effects, and finally found that novel pyrazolo[4,3-d]pyrimidine derivatives of the present invention have excellent antihyperlipidemic effects, and yet they have functions to reduce LDL-cholesterol and increase HDL-cholesterol. Further, they are highly safe without subsidiary ill effects against liver such as hepatomegaly. The present invention has been accomplished on the basis of these discoveries.

The following compounds have been known as the closest to the compounds of the present invention.

Namely, with respect to 3,7-dihydroxy-pyrazolo[4,3-d]pyrimidines with the nitrogen atom at the 2-position substituted by an optionally substituted hydrocarbon group, there have been known only 2-methyl-, phenyl- or substituted phenyl-3,7-dihydroxy-pyrazolo[4,3-d]pyrimidine [H. Ochi and T. Miyasaka, Chem. Parm. Bull., 31, 1228(1983)] and 2-phenyl-3,5,7-trihydroxy-pyrazolo[4,3-d]pyrimidine [Gerhard Siewert, Arch. Pharm., 278, 327–333(1940)(Chemical Abstract 35, 3232$^6$)].

3-Oxy substituted-pyrazolo[4,3-d]pyrimidine with the nitrogen atom at the 2-position substituted by an optionally substituted hydrocarbon group has not been known.

From the viewpoint of the pharmacological activities, the closest to the compounds of the present invention, with respect to pyrazolo[3,4-d]pyrimidines, is 1H-pyrazolo[3,4-d]pyrimidine-4-amine which is known to have a function to reduce serum lipid [Science, 193,903(1976), J. Lipid Res., 12, 596(1971)]. However, no such an activity has been reported with respect to pyrazolo[4,3-d]pyrimidines.

The present inventors have synthesized novel compounds of the present invention and studied their pharmacological activities, whereupon it has been found that the new compounds have antihyperlipidemic effects. Thus, the present invention has been accomplished.

Namely, the novel pyrazolo[4,3-d]pyrimidines having antihyperlipidemic effects according to the present invention, are represented by the formula:

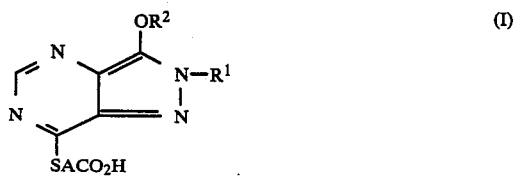
(I)

wherein $R^1$ is lower alkyl or phenyl which is unsubstituted or substituted by lower alkyl, lower alkoxy or halogen; $R^2$ is a saturated or unsaturated, straight chain or branched aliphatic group having from 2 to 22 carbon atoms or phenyl-lower alkyl with the phenyl group unsubstituted or substituted by lower alkyl, lower alkoxy or halogen; and A is an alkylene group having from 1 to 3 carbon atoms which is unsubstituted or substituted by methyl, or a pharmaceutically acceptable salt thereof.

The present invention also provides a process for producing a compound of the formula I or its pharmaceutically acceptable salt, which comprises reacting a pyrazolo[4,3-d]pyrimidine derivative having the formula:

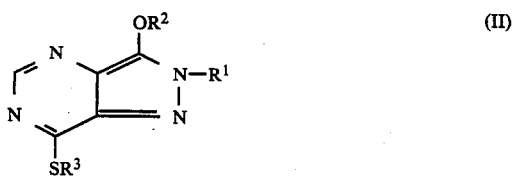
(II)

wherein $R^1$ and $R^2$ are as defined above, and $R^3$ is $ACO_2R^{31}$ (wherein A is as defined above and $R^{31}$ is lower alkyl having from 1 to 4 carbon atoms, benzyl or phenyl), $CH_2CO$-phenyl, a saturated or unsaturated, straight chain or branched aliphatic group having from 1 to 16 carbon atoms or phenyl-lower alkyl with the phenyl group unsubstituted or substituted by lower alkyl or halogen, with a mercaptoalkyl carboxylic acid having the formula:

HSACO$_2$H     (III)

wherein A is defined above; or hydrolyzing a pyrazolo[4,3-d]pyrimidine derivative having the formula:

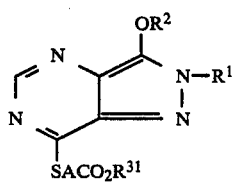

(IV)

wherein $R^1$, $R^2$, A and $R^{31}$ are as defined above, with an acid or base, followed by neutralization.

Further, the present invention provides an antihyperlidemic or antiatherosclerotic agent which comprises an effective amount of a compound of the formula I or a pharmaceutically acceptable salt thereof, and a pharmaceutically, acceptable carrier.

Now, the present invention will be described in detail with reference to the preferred embodiments.

Referring to the formulas I to IV, various substituents will be described.

As the lower alkyl for $R^1$, alkyl having from 1 to 4 carbon atoms, such as methyl, ethyl, n-propyl, iso-propyl, n-butyl, t-butyl or sec-butyl, is preferred. Among them, methyl is particularly preferred.

The substituent on the phenyl for $R^1$, includes lower alkyl such as methyl, ethyl, iso-propyl or t-butyl, lower alkoxy such as methoxy, ethoxy or iso-propoxy, and halogen such as chlorine, bromine, fluorine or iodine.

The saturated or unsaturated, straight chain or branched aliphatic group having from 2 to 22 carbon atoms for $R^2$, preferably is a saturated or unsaturated, straight chain aliphatic group having from 14 to 20 carbon atoms, more preferably an unsaturated, straight chain aliphatic group having from 14 to 20 carbon atoms, such as oleyl, linoleyl or linolenyl.

As the substituent on the phenyl group of the substituted phenyl-lower alkyl for $R^2$, there may be mentioned lower alkyl such as methyl, ethyl, iso-propyl or t-butyl, lower alkoxy such as methoxy, ethoxy or iso-propoxy, and halogen such as chlorine, bromine, fluorine or iodine.

The alkylene for A includes —CH$_2$—, —(CH$_2$)$_2$—, —(CH$_2$)$_3$—, —CH(CH$_3$)— and —C(CH$_3$)$_2$—.

As the pharmaceutically acceptable salt of the compound of the formula I, there may be mentioned an inorganic salt such as a sodium salt, a calcium salt or a magnesium salt, or an organic salt such as an organic amine salt.

The pyrazolo[4,3-d]pyrimidines of the formula I according to the present invention, can be prepared in accordance with the following reaction schemes.

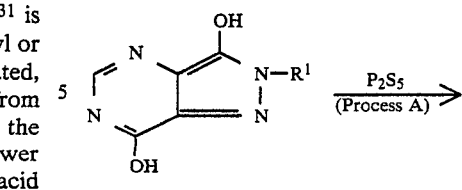

(V)

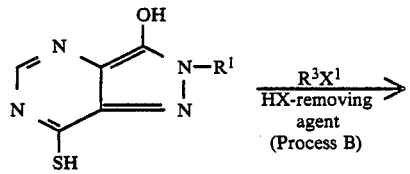

(IV)

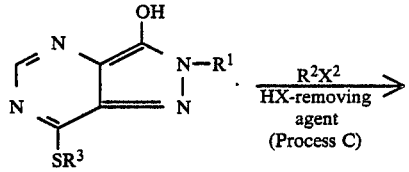

(III)

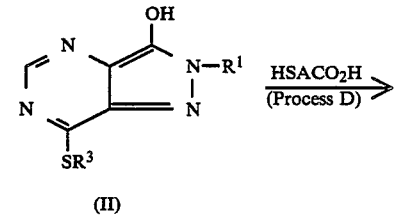

(II)

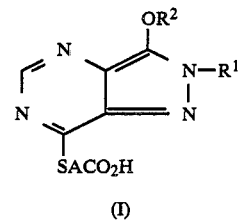

(I)

When $R^3 = ACO_2R^{31}$ in the compound of the formula II:

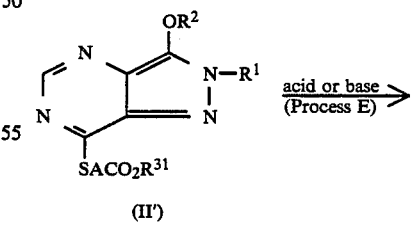

(II')

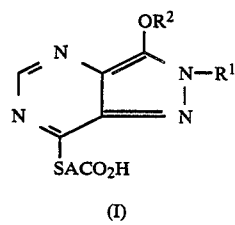

(I)

In the above formulas, each of $X^1$ and $X^2$ is halogen, alkylsulfonyloxy or phenylsulfonyloxy which is unsubstituted or substituted by halogen such as chlorine, or lower alkyl such as methyl, and $R^1$, $R^2$, $R^3$, $R^{31}$ and A are as defined above.

Process A is a process step to convert the hydroxy group at the 7-position of 3,7-dihydroxy pyrazolo[4,3-d]pyrimidine to a mercapto group. This reaction is conducted in an organic solvent such as pyridine by reacting phosphorus pentasulfide under heating.

Process B is a step of preparing a thioether compound by the reaction of the mercapto group at the 7-position with a halide, an optionally substituted phenylsulfonyloxy compound or an alkylsulfonyloxy compound. This reaction is conducted in water or an alcoholic organic solvent such as methanol or ethanol, or in a mixture of such solvents, at room temperature or under heating, in the presence of an acid binding agent such as sodium carbonate or potassium carbonate. Alternatively, the reaction may be conducted in aqueous ammonia at room temperature.

Process C is a step of forming an ether bond by the reaction of the hydroxy group at the 3-position with a halide, an optionally substituted phenylsulfonyloxy compound or an alkylsulfonyloxy compound. This reaction is conducted in an organic solvent such as benzene, toluene, xylene, dimethylformamide, dimethylsulfoxide, dioxane, tetrahydrofuran, methanol or ethanol, at room temperature or under heating in the presence of an acid binding agent such as potassium carbonate, sodium carbonate, a tertiary amine or pyridine. Alternatively, the reaction may be conducted in a solvent mixture comprising water and an organic solvent hardly soluble in water such as chloroform, methylene chloride, benzene or toluene or a mixture of such organic solvents, in the presence of an acid binding agent such as potassium carbonate, sodium carbonate, sodium hydroxide or potassium hydroxide and a phase transfer catalyst such as 18-crown-6.

Process D is a step of substituting the $SR^3$ group at the 7-position by $HSACO_2H$, and is conducted in the absence of a solvent or in a solvent such as benzene, ethyl ether, tetrahydrofuran, dioxane, hexane, acetone, chloroform or dichloromethane. Further, the reaction may be facilitated by the presence of a base such as triethylamine or pyridine.

Process E is a process which is employed when $R^3$ in the formula II is $ACO_2R^{31}$. For instance, when $R^{31}$ is tert-butyl, the reaction may be conducted in trifluoroacetic acid at room temperature under stirring. Likewise, when $R^{31}$ is methyl or ethyl (particularly methyl), the reaction may be conducted in methanol, ethanol or a solvent mixture of methanol or ethanol with water by reacting a base such as lithium hydroxide, sodium hydroxide or potassium hydroxide.

The compounds of the formulas II and III are industrially useful as they are used as intermediates for the compounds of the formula I having antihyperlipidemic effects, as described in Processes D and E.

The compounds of the formula I of the present invention exhibit remarkable antihyperlipidemic effects, effects to raise the ratio of high density lipoprotein cholesterol in serum to total cholesterol in serum and eventually antiatherosclerotic effects. They may be formulated into various suitable formulations depending upon the manner of the administration.

The pharmaceutical composition of the present invention comprises an effective amount of the compound of the formula I or a pharmaceutically acceptable salt thereof and a pharmaceutically acceptable carrier. The effective amount is usually at least 5% by weight, based on the total composition. As the pharmaceutically acceptable carrier, there may be mentioned a pharmaceutically acceptable binder such as a syrup, gum arabic, gelatin, sorbitol, tragacanth gum or polyvinylpyrrolidone (molecular weight of e.g. about 25,000); an excipient such as lactose, sugar, corn starch, calcium phosphate, sorbitol or glycine; a lubricant such as magnesium stearate, talc, polyethylene glycol or silica; or a disintegrator such as potato starch. By properly selecting the carrier, the pharmaceutical composition of the present invention may be formulated into powders, granules, tablets or capsules. It is preferably administered orally. However, the manner of administration is not restricted to oral administration, and non-oral administration such as percutaneous administration, injection (through an intravenous, subcutaneous or intramuscular route) or rectal administration may be employed. For instance, it may be administered as a suppository as combined with oily base material such as cacao butter, polyethylene glycol, lanolin or fatty acid triglyceride.

The daily dose of the compound of the formula I is from 0.01 to 2.0 g, preferably from 0.1 to 1.5 g, for an adult. It is administered from once to three times per day. The dose may of course be varied depending upon the age, the weight or the condition of illness of the patient.

Now, the present invention will be described in further detail with reference to test examples for the antihyperlipidemic effects of the compounds of the formula I, working examples [Example A Nos. for the synthesis of the intermediates of the formulas II, II', III and IV by the above-mentioned Processes A, B, C and D and Example Nos. for the synthesis of the compounds of the formula I by Processes D and E]and formulation examples.

In the following description, Me means methyl; Et means ethyl; Pr means propyl; Bu means butyl; and Ph means phenyl.

Test 1

The antihyperlipidemic activity in emulsion-induced hyperlipidemic rats:

Male S.D. rats weighing 80–90 g (4 weeks old) were used. They were divided into groups of 5 to 6 rats each. The test compounds suspended in 0.5% CMC-Na(carboxymethyl cellulose sodium salt) were given to the rats in a daily dose of 4 ml/kg via stomach tube every 10:00 a.m. After 30 min., lipids emulsion having the following composition was orally given to the rats in an amount of 2.5 ml per rat.

| Composition of emulsion: | |
|---|---|
| Cholesterol | 22.5 g |
| Cholic acid sodium salt | 10.0 g |
| Sucrose | 90.0 g |
| Olive oil | 150.0 g |
| Water | x ml |
| Final volume | 300.0 ml |

During the experimental period of 3 days, the rats were fed on a standard commercial diet and water ad libitum. At the end of the period, the rats were fasted for 16 hours and then blood samples were obtained from inferior vena cava. The total cholesterol and HDL cholesterol were measured.

The weight of the liver was measured. To the control group, only the aqueous CMC-Na solution and the lipids emulsion were given.

where E is the liver weight (g) per 100 g of the body weight of the control group, and F is the liver weight (g) per 100 g of the body weight of the group to which the therapeutic agent was administered.

The test results are shown in Table 1.

TABLE 1

$$\text{structure with } OR^2, N-R^1, SACO_2H$$

The effects of the compounds of the formula I for the reduction of serum Chol. and over the serum HDL—Chol. and the liver weight.

| Example No. | A | $R^1$ | $R^2$ | Dose (mg/kg) | Reduction rate of serum Chol. (%) | Increase rate of serum HDL—Chol. (%) | Degree of hepatomegaly (%) |
|---|---|---|---|---|---|---|---|
| 2 | $CH_2$ | $CH_3$ | $C_{16}H_{33}$ | 300 | 41.0 | 14.1 | 9.2 |
| 1 | $CH_2$ | $CH_3$ | $C_{18}H_{33}$ (linoleyl) | 300 | 73.5 | −17.7*2 | 17.8 |
| 1 | $CH_2$ | $CH_3$ | $C_{18}H_{33}$ (linoleyl) | 50 | 35.5 | 13.4 | 7.6 |
| 1 | $CH_2$ | $CH_3$ | $C_{18}H_{33}$ (linoleyl) | 25 | 25.6 | 21.8 | 6.0 |
| Clofibrate (Reference compound)*1 | | | | 300 | 35.6 | −18.2*2 | 12.1 |

*1Clofibrate Cl—⟨phenyl⟩—OCCO₂Et with Me groups

*2The minus value represents a reduction rate.

The fractionation of lipoproteins was conducted by a dextran sulfate-MgCl₂ precipitation method.

Cholesterol in serum was measured by means of a cholesterol measuring kit (Cholesterol C-Test Wako, manufactured by Wako Junyaku Co., Ltd.), and cholesterol in HDL was measured by means of NC Hi-Set, manufactured by Nippon Chemiphar Co., Ltd.

In the following description, cholesterol is referred to as "Chol".

Further, the reduction rate of Chol was calculated by the following equation.

$$\text{Reduction rate (\%)} = \frac{A - B}{A} \times 100$$

where A is the amount of serum Chol (mg/dl) of the control group, and B is the amount of serum Chol (mg/dl) of the group to which the therapeutic agent was administered.

Likewise, the increase rate of HDL-Chol was calculated by the following equation.

$$\text{Increase rate (\%)} = \frac{D - C}{C} \times 100$$

where C is the amount of serum HDL-Chol (mg/dl) of the control group, and D is the amount of serum HDL-Chol (mg/dl) of the group to which the therapeutic agent was administered.

The degree of hepatomegaly (i.e. the change rate of the liver weight) was calculated by the following equation.

$$\text{Degree of hepatomegaly (\%)} = \frac{F - E}{E} \times 100$$

Test 2

Acute toxicity

The test compounds dissolved in corn oil were administered p.o. to male ddY mice. The acute toxicity was determined based on the mortality after seven days. In respect of the compounds of Examples 1 and 2 of the present invention, the mortality was 0% even at a dose of as high as 1000 mg/kg by oral administration.

EXAMPLE A-1

2-Methyl-3-hydroxy-7-mercapto-pyrazolo[4,3-d]pyrimidine $$\text{structure with } OH, NMe, SH$$

50 g of 2-methyl-3,7-dihydroxy-pyrazolo[4,3-d]pyrimidine was suspended in 500 ml of dry pyridine, and 140 g of phosphorus pentasulfide was gradually added to this suspension while thoroughly stirring the suspension. The mixture was thoroughly stirred until the heat generation terminated and the temperature of the mixture dropped to a level close to room temperature. Then, the mixture was stirred under heating at a temperature of from 80° to 100° C. for about 1.5 hours to obtain a uniform brown solution. Pyridine was distilled off under reduced pressure. To the viscous oily residue, 500 ml of water was added, and the mixture was thoroughly shaken and mixed to obtain a uniform solution. The solution was heated on a hot water bath for 1.5 hours. After cooling, the solution was acidified with hydrochloric acid, and the precipitates thereby formed were collected by filtration, and washed with water to obtain a yellowish brown powder. The powder was dissolved in a saturated sodium hydrogencarbonate aqueous solution, and insoluble matters were removed by filtration. The filtrate was acidified with hydrochloric acid, and a yellowish brown powder thereby precipitated, was collected by filtration, washed with water and dried.

Melting point: over 320° C.
Yield: 36 g (60%)
pmr (d$_6$-DMSO) δppm: 3.70 (s, 3H), 7.80 (s, 1H)

EXAMPLE A-2

2-Methyl-3-hydroxy-7-ethoxycarbonylmethylthio-pyrazolo[4,3-d]pyrimidine

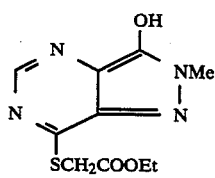

10 g of 2-methyl-3-hydroxy-7-mercapto-pyrazolo[4,3-d]pyrimidine and 8.36 g of anhydrous potassium carbonate were dissolved in 100 ml of water, and after an addition of 8.08 g of ethyl bromoacetate, the mixture was stirred at room temperature for 4 hours. After confirming the completion of the reaction by means of thin layer chromatography, the reaction mixture was shaked with chloroform, whereby by-products were extracted to the chloroform layer and thus removed. The aqueous layer was neutralized with 1:1 hydrochloric acid to bring the pH to a level of from 3 to 4. The precipitated crystals were collected by filtration and then washed with water. Then, the crystals were recrystallized from chloroform-acetone.

Yield: 9.24 g (62.7%), yellow crystals
Melting point: 178°–182° C.
pmr (CDCl$_3$) δppm: 1.25 (t, 3H, J=8 Hz), 4.0 (s, 3H), 4.13 (s, 2H), 4.20 (q, 2H, J=8 Hz) 8.43 (s, 1H), 10.3 (s, 1H).

EXAMPLE A-3

2-Methyl-3-hydroxy-7-methoxycarbonylmethylthio-pyrazolo[4,3-d]pyrimidine

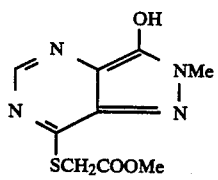

The desired product was obtained by conducting the reaction and treatment in the same manner as in Example A-2 except that methyl bromoacetate was used instead of ethyl bromoacetate in Example A-2.

Yield: 43.4%
Melting point: 195°–196° C. (recrystallized from chloroform-acetone), orange powder
pmr (CDCl$_3$) δppm: 3.78 (s, 3H), 4.04 (s, 3H), 4.24 (s, 2H), 8.58 (s, 1H)

EXAMPLE A-4

2-Methyl-3-hydroxy-7-t-buthoxycarbonylmethylthio-pyrazolo[4,3-d]pyrimidine

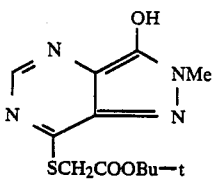

The desired product was obtained by conducting the reaction and treatment in the same manner as in Example A-2 except that t-butyl bromoacetate was used instead of ethyl bromoacetate in Example A-2.

Yield: 62.6%
Melting point: 168.5°–169.5° C. (recrystallized from acetone)
pmr (CDCl$_3$) δppm: 1.45 (s, 9H), 4.00 (s, 3H), 4.05 (s, 2H), 8.40 (s, 1H), 14.00 (s, 1H)

EXAMPLE A-5

2-Methyl-3-hydroxy-7-benzylthio-pyrazolo[4,3-d]pyrimidine

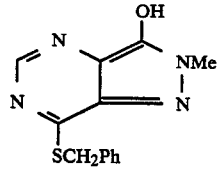

1.82 g of 2-methyl-3-hydroxy-7-mercapto-pyrazolo[4,3-d]pyrimidine was dissolved in 30 ml of aqueous ammonia, and after an addition of 2.05 g of benzyl bromide, the mixture was stirred at room temperature for 89 hours. By means of a rotary evaporator, ammonia gas was distilled off at room temperature. Then, the aqueous solution was acidified with hydrochloric acid and extracted with chloroform. The chloroform layer was dried over anhydrous magnesium sulfate, and then evaporated to dryness. The remaining solid was recrystallized from acetone. Yield: 45.4% Melting point: 197°–199° C., orange crystals
pmr (d$_6$-DMSO) δppm 3.78 (s, 3H), 4.65 (s, 2H), 7.2–7.7 (m, 5H), 8.68 (s, 1H)

EXAMPLE A-6

2-Methyl-3-linoleyloxy-7-methoxycarbonymethylthio-pyrazolo[4,3-d]pyrimidine

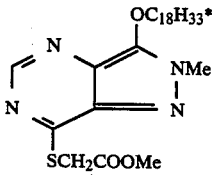

wherein C$_{18}$H$_{33}$*=linoleyl.

1.0 g of 2-methyl-3-hydroxy-7-methoxycarbonylmethylthio-pyrazolo[4,3-d]pyrimidine obtained in Example A-2, was dissolved in 10 ml of dry dimethylacetamide, and 0.54 g of anhydrous potassium carbonate was added thereto. After a dropwise addition of 1.82 g of linoleyl tosylate at room temperature in a nitrogen atmosphere, the mixture was heated at 60° C. for 2 hours. After confirming the completion of the reaction by means of thin layer chromatography, water was added to the reaction mixture under cooling, and the mixture was extracted with hexane. The hexane layer was washed with water and dried over magnesium sulfate. Then, the solvent was completely distilled off. The oily residue was subjected to silica gel chromatography (eluant: ethyl acetate/benzene) to obtain the desired product.

Yield: 57.1%, light yellow oily substance pmr (CDCl3) δppm: 0.8–3.0 (m, 31H), 3.76 (s, 3H), 3.96 (s, 3H), 4.16 (s, 2H), 5.36 (m, 2H), 8.49 (s, 1H)

EXAMPLE A-7

2-Methyl-3-cetyloxy-7-methoxycarbonylmethylthio-pyrazolo[4,3-d]pyrimidine

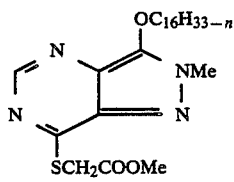

The desired product was obtained by conducting the reaction and treatment in the same manner as in Example A-6 except that cetyl tosylate was used instead of linoleyl tosylate in Example A-6.

Yield: 73.8%

Melting point: 58.5°–59.5° C., light yellow powder (recrystallized from hexane)

pmr (CDCl3) δppm: 0.7–2.1 (m, 31H), 3.76 (s, 3H), 3.86 (s, 3H), 4.16 (s, 2H), 4.89 (t, 2H, J=6 Hz), 8.49 (s, 1H)

Mass (m/e): 478 (M+), 373 (M+—SCH2CO2Me), 254(M+—C16H32)

EXAMPLE A-8

2-Methyl-3-linoleyloxy-7-t-butoxycarbonylmethylthio-pyrazolo[4,3-d]pyrimidine

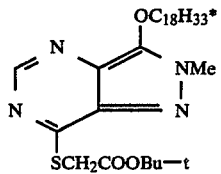

wherein $C_{18}H_{33}$* = linoleyl.

The desired product was obtained by conducting the reaction and treatment in the same manner as in Example A-6 except that 2-methyl-3-hydroxy-7-t-butoxycarbonylmethylthio-pyrazolo[4,3-d]pyrimidine was used instead of 2-methyl-3-hydroxy-7-methoxycarbonyl-methylthio-pyrazolo[4,3-d]pyrimidine in Example A-6.

Yield: 76.0%, light yellow oily substance pmr (CDCl3) δppm: 0.7–2.9 (m, 27H), 1.47 (s, 9H), 3.96 (s, 3H), 4.04 (s, 2H), 4.89 (t, 2H, J=6 Hz), 5.3–5.5 (m, 4H), 8.48 (s, 1H)

Mass (m/e): 544 (M+), 488, 429, 397, 296, 240

EXAMPLE A-9

2-Methyl-3-cetyloxy-7-benzylthio-pyrazolo[4,3-d]pyrimidine

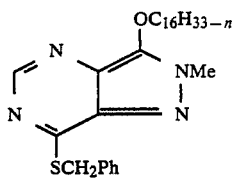

The desired product was obtained by conducting the reaction and treatment in the same manner as in Example A-6 except that 2-methyl-3-hydroxy-7-benzylthio-pyrazolo[4,3-d]pyrimidine was used instead of 2-methyl-3-hydroxy-7-methoxycarbonylmethylthio-pyrazolo[4,3-d]pyrimidine and cetyl tosylate was used instead of linoleyl tosylate in Example A-6.

Yield: 71%

Melting point: 63.0°–64.0° C.

pmr (CDCl3) δppm 0.7–2.0 (m, 31H), 3.93 (s, 3H), 4.62 (s, 2H), 4.86 (t, 2H, J=6 Hz), 7.1–7.6 (m, 5H), 8.54 (s, 1H)

Mass (m/e): 496 (M+), 91

EXAMPLE A-10

2-Methyl-3-linoleyloxy-7-ethoxycarbonylmethylthio-pyrazolo[4,3-d]pyrimidine

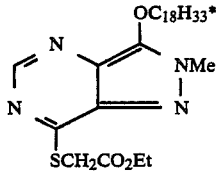

wherein $C_{18}H_{33}$* = linoleyl.

The desired product was obtained by conducting the reaction and treatment in the same manner as in Example A-6 except that 2-methyl-3-hydroxy-7-ethoxycarbonylmethylthio-pyrazolo[4,3-d]pyrimidine was used instead of 2-methyl-3-hydroxy-7-methoxycarbonyl-methylthio-pyrazolo[4,3-d]pyrimidine in Example A-6.

Yield: 80%, slightly yellow oily substance

Melting Point: 22.0°–25.0° C.

pmr (CDCl3) δppm: 0.8–2.2 (m, 28H), 2.6–2.9 (m, 2H), 3.96 (s, 3H), 4.15 (s, 2H), 4.22 (q, 2H, J=7 Hz), 4.89 (t, 2H, J=6.5 Hz), 5.2–5.6 (m, 4H), 8.48 (s, 1H)

Mass (m/e): 516 (M+), 429 (M+—CH2CO2Et), 397 (M+—SCH2CO2Et), 268 (M+—C18H32)

EXAMPLE 1

2-Methyl-3-linoleyloxy-7-carboxymethylthio-pyrazolo[4,3-d]pyrimidine

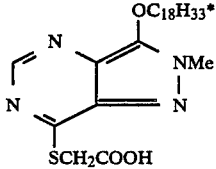

wherein $C_{18}H_{33}$* = linoleyl.

(Synthesis 1)

1.00 g of 2-methyl-3-linoleyloxy-7-methoxycarbonyl-methylthio-pyrazolo[4,3-d]pyrimidine obtained in Example A-6, was dissolved in 10 ml of dry methanol. To this solution, a solution obtained by dissolving 0.08 g of lithium hydroxide monohydrate in 10 ml of methanol, was added, and the mixture was stirred in a nitrogen atmosphere at room temperature for 2 hours. To the reaction solution, chloroform was added, and the mixture was adjusted to pH4 with dilute hydrochloric acid. Then, the chloroform layer obtained by liquid separation, was washed with a saturate sodium chloride aqueous solution and dried over magnesium sulfate. The solvent was distilled off by an evaporator, and the oily residue was subjected to silica gel column chromatogaphy (eluant:methanol/chloroform) to obtain the desired product.

Yield: 26.6%
Melting Point: 39°–42° C.
pmr (CDCl$_3$) $\delta$ppm: 0.7–2.9 (m, 27H), 3.88 (s, 3H), 3.98 (s, 2H), 4.90 (t, 2H, J=6 Hz), 5.3–5.5 (m, 4H), 8.50 (s, 1H)
Mass (m/e): 488 (M+), 470 (M+—H$_2$O ), 397 (M+—SCH$_2$CO$_2$H), 240 (M+—C$_{18}$H$_{33}$)
IR(KBr-disk) $\nu_{C=O}$ 1725 cm$^{-1}$, (s)

(Synthesis 2)

1.09 g of 2-methyl-3-linoleyloxy-7-t-butoxycarbonyl-methylthio-pyrazolo[4,3-d]pyrimidine obtained in Example A-8, was dissolved in 2 g of trifluoroacetic acid, and the solution was stirred in a nitrogen atmosphere at room temperature for 9 hours. To the reaction solution, chloroform was added, and the mixture was washed with a saturated sodium chloride aqueous solution. The chloroform layer was dried over magnesium sulfate, and the solvent was distilled off by an evaporator. The oily residue was treated in the same manner as in Synthesis 1 to obtain 0.83 g (yield: 85.0%) of the desired product.

(Synthesis 3)

2.00 g of 2-methyl-3-linoleyloxy-7-ethoxycarbonyl-methylthio-pyrazolo[4,3-d]pyrimidine obtained in Example A-10 and 3.57 g of thioglycolic acid were dissolved in 3 ml of chloroform, and the solution was cooled with ice. To this solution, 7.84 g of triethylamine was gradually added, and the mixture was further stirred in a nitrogen atmosphere at room temperature for 42 hours. To the reaction solution, chloroform was added, and then the chloroform layer was washed with dilute hydrochloric acid and adjusted to pH4. Further, the solution was washed with a saturated sodium chloride aqueous solution, and dried over magnesium sulfate. The solvent was distilled off by an evaporator. The oily residue was treated in the same manner as in Synthesis 1 to obtain 1.04 g (yield: 55%) of the desired product.

EXAMPLE 2

2-Methyl-3-cetyloxy-7-carboxymethylthio-pyrazolo[4,3-d]pyrimidine

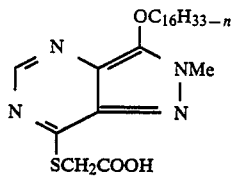

(Synthesis 1)

The desired product was obtained by conducting the reaction and treatment in the same manner as in Synthesis 1 of Example 1 by using 2-methyl-3-cetyloxy-7-methoxycarbonylmethylthio-pyrazolo[4,3-d]pyrimidine obtained in Example A-7

Yield: 79.7%
Melting point: 75°–78° C. (recrystallized from hexane)
pmr (CDCl$_3$) $\delta$ppm: 0.7–2.0 (m, 31H), 3.98 (s, 3H), 4.06 (s, 2H), 4.90 (t, 2H, J=6 Hz), 8.50 (s, 1H)
Mass (m/e): 464 (M+), 447 (M+—OH), 239 (M+—C$_{16}$H$_{33}$—n) 166, 44

(Synthesis 2)

The desired product was obtained by conducting the reaction and treatment in the same manner as in Synthesis 3 of Example 1 by using 2-methyl-3-cetyloxy-7-benzylthio-pyrazolo[4,3-d]pyrimidine obtained in Example A-9.

Yield: 75%

EXAMPLE 3

Sodium salt of 2-methyl-3-linoleyloxy-7-carboxymethylthio-pyrazolo[4,3-d]pyrimidine

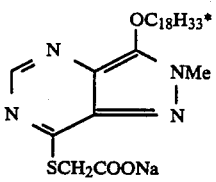

wherein C$_{18}$H$_{33}$=linoleyl.

2.44 g of 2-methyl-3-linoleyloxy-7-carboxymethylthio-pyrazolo[4,3-d]pyrimidine obtained in Example 1 was dissolved in 8 ml of methanol dehydrated by molecular sieve. To this solution, 0.79 g of dry sodium carbonate powder was added, and the mixture was stirred in a nitrogen atmosphere at room temperature for 5 hours. The remaining excess sodium carbonate was removed by filtration, and the solvent was distilled off under reduced pressure at room temperature to obtain 2.41 g (94.5%) of the desired product as a yellow wax-like substance.

pmr (d$_6$-DMSO) $\delta$ppm: 0.7–2.8 (m, 27H), 3.90 (s, 3H), 3.93 (s, 2H), 4.80 (t, 2H, J=6 Hz), 5.2–5.5 (m, 4H), 8.25 (s, 1H)
IR(KBr-disk) $\nu_{(CO_2)^-}$ 1590 cm$^{-1}$ Now, there will be given Examples for formulations containing antihyperlipidemic compounds of the present invention.

FORMULATION EXAMPLE 1
TABLETS

| Composition (4,000 tablets) | |
|---|---|
| Compound of Example 1 | 500 (g) |
| Potato starch | 334 |
| Carboxymethyl cellulose | 87.5 |
| Polyvinyl alcohol | 61 |
| Magnesium stearate | 17.5 |
| | 1,000 |

The above ingredients in the respective amounts were introduced into a twin shell mixer and uniformly mixed. This powder mixture was tableted by a direct compression method to obtain tablets having a weight of 250 mg per tablet.

FORMULATION EXAMPLE 2
CAPSULES

| Composition (1,000 capsules) | |
|---|---|
| Compound of Example 1 | 250 (g) |
| Olive oil | 250 |
| | 500 |

The above ingredients in the respective amounts were uniformly mixed. This powder mixture was packed in soft gelatin capsules in an amount of 500 mg per capsule, and dried.

FORMULATION EXAMPLE 3
GRANULES

| Composition (1,000 packages) | |
|---|---|
| Compound of Example 2 | 100 (g) |
| Silicic anhydride | 80 |
| Crystalline cellulose | 180 |
| Lactose | 130 |
| Magnesium stearate | 10 |
| | 500 |

The above ingredients in the respective amounts were uniformly mixed, then granulated and packaged in an amount of 500 mg per package.

FORMULATION EXAMPLE 4
SUPPOSITORY

| Composition (1,000 pcs) | |
|---|---|
| Compound of Example 2 | 200 (g) |
| Cacao butter | 1,000 |
| | 1,200 |

The above ingredients in the respective amounts were uniformly melted at 38° C., and poured into a casting mold for suppository which was preliminarily cooled. The weight per piece of suppository was 1.2 g.

What is claimed is:

1. A pyrazolo[4,3-d]pyrimidine derivative having the formula:

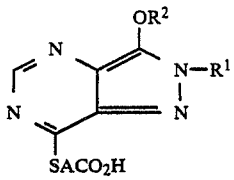

wherein $R^1$ is lower alkyl or phenyl which is unsubstituted or substituted by a lower alkyl, a lower alkoxy or a halogen substituent; $R^2$ is a saturated or unsaturated, straight chain or branched aliphatic group having from 2 to 22 carbon atoms or phenyl-lower alkyl with the phenyl group unsubstituted or substituted by a lower alkyl, a lower alkoxy or a halogen substituent; and A is an alkylene group having from 1 to 3 carbon atoms which is unsubstituted or substituted by no more than two methyl groups, or a pharmaceutically acceptable salt thereof.

2. The pyrimidine derivative according to claim 1, wherein $R^1$ is alkyl having from 1 to 4 carbon atoms, and $R^2$ is a saturated or unsaturated, straight chain aliphatic group having from 14 to 20 carbon atoms.

3. The pyrimidine derivative according to claim 1, wherein $R^1$ is methyl, and $R^2$ is a saturated or unsaturated, straight chain aliphatic group having from 14 to 20 carbon atoms.

4. The pyrimidine derivative according to claim 1, wherein $R^1$ is methyl, and $R^2$ is a saturated, straight chain aliphatic group having from 14 to 20 carbon atoms.

5. The pyrimidine derivative according to claim 1, wherein $R^1$ is methyl, $R^2$ is oleyl, linoleyl or linolenyl, and A is $-CH_2-$, $-CH(CH_3)-$, $-C(CH_3)_2-$, $-(CH_2)_2-$ or $-(CH_2)_3-$.

6. The pyrimidine derivative according to claim 1, wherein $R^1$ is methyl, $R^2$ is oleyl, linoleyl or linolenyl, and A is $-CH_2-$, $-(CH_2)_2-$ or $-(CH_2)_3-$.

7. The pyrimidine derivative according to claim 1, wherein $R^1$ is methyl, $R^2$ is linoleyl, and A is $-CH_2-$.

8. The pyrimidine derivative according to claim 1, wherein $R^1$ is methyl, $R^2$ is oleyl, and A is $-CH_2-$.

9. The pyrimidine derivative according to claim 1, wherein $R^1$ is methyl, $R^2$ is linolenyl, and A is $-CH_2-$.

10. The pyrimidine derivative according to claim 1, wherein $R^1$ is methyl, $R^2$ is $C_{16}H_{33}$ and A is $-CH_2-$.

11. An antihyperlipidemic or antiatherosclerotic agent comprising a therapeutically effective amount of the pyrimidine derivative of the formula I as defined in claim 1 or a pharmaceutically acceptable salt thereof, and a pharmaceutically acceptable carrier.

12. The antihyperlipidemic or antiatherosclerotic agent according to claim 11, wherein $R^1$ is methyl, $R^2$ is oleyl, linoleyl or linolenyl, and A is $-CH_2-$, $-(CH_2)_2-$ or $-(CH_2)_3-$.

* * * * *